United States Patent
Dines et al.

(10) Patent No.: US 10,377,983 B2
(45) Date of Patent: Aug. 13, 2019

(54) METHODS FOR THE PRODUCTION OF DIATOM BIOMASS

(71) Applicant: FERMENTALG, Libourne (FR)

(72) Inventors: Mark Humphrey Dines, Auckland (NZ); Hywel David Griffiths, Auckland (NZ); Moreland David Gibbs, Auckland (NZ)

(73) Assignee: FERMENTALG, Libourne (FR)

( * ) Notice: Subject to any disclaimer, the term of this patent is extended or adjusted under 35 U.S.C. 154(b) by 0 days.

(21) Appl. No.: 15/838,772

(22) Filed: Dec. 12, 2017

(65) Prior Publication Data
US 2018/0230419 A1    Aug. 16, 2018

Related U.S. Application Data

(62) Division of application No. 14/907,846, filed as application No. PCT/NZ2013/000213 on Nov. 21, 2013, now Pat. No. 9,879,218.

(30) Foreign Application Priority Data
Aug. 1, 2013 (NZ) ........................................ 613593

(51) Int. Cl.
| | | |
|---|---|---|
| C12P 7/64 | (2006.01) | |
| C12N 1/12 | (2006.01) | |
| A61K 31/232 | (2006.01) | |
| C11B 11/00 | (2006.01) | |
| A61K 31/202 | (2006.01) | |

(Continued)

(52) U.S. Cl.
CPC .............. *C12N 1/12* (2013.01); *A23K 20/158* (2016.05); *A23L 33/12* (2016.08); *A61K 31/202* (2013.01); *A61K 31/232* (2013.01); *A61K 31/685* (2013.01); *A61K 36/00* (2013.01);
(Continued)

(58) Field of Classification Search
CPC ..................................................... C12P 7/6472
See application file for complete search history.

(56) References Cited

U.S. PATENT DOCUMENTS

| | | |
|---|---|---|
| 5,244,921 A | 9/1993 | Kyle et al. |
| 7,939,710 B1 | 5/2011 | Apt et al. |

(Continued)

FOREIGN PATENT DOCUMENTS

| | | |
|---|---|---|
| WO | WO-2005/021735 A1 | 3/2005 |
| WO | WO-2006/085144 A2 | 8/2006 |

(Continued)

OTHER PUBLICATIONS

Brown et al., A relationship between growth and lipid accumulation in Candida curvata D. *J. Ferm. Bioeng.* 68:344-52 (1989).
(Continued)

*Primary Examiner* — Rosanne Kosson
(74) *Attorney, Agent, or Firm* — Marshall, Gerstein & Borun LLP (57) ABSTRACT

The invention relates to methods of producing a diatom biomass. More particularly, the invention relates to methods to produce a diatom biomass using a continuous culture to produce a volumetric production rate of biomass of at least 20 g dry weight/L/day, wherein the culture medium is designed to provide the essential nutrients to maintain the diatom in log phase growth. In a preferred embodiment the biomass comprises highly unsaturated fatty acid.

9 Claims, 2 Drawing Sheets

(51) Int. Cl.
  A61K 31/685  (2006.01)
  A61K 36/00   (2006.01)
  A23K 20/158  (2016.01)
  A23L 33/12   (2016.01)

(52) U.S. Cl.
  CPC .............. *C11B 11/00* (2013.01); *C12P 7/6472* (2013.01); *A23V 2002/00* (2013.01); *Y02A 50/406* (2018.01)

(56) References Cited

U.S. PATENT DOCUMENTS

| | | |
|---|---|---|
| 2010/0021555 A1 | 1/2010 | Geiringer et al. |
| 2010/0086979 A1 | 4/2010 | Kiy et al. |

FOREIGN PATENT DOCUMENTS

| | | |
|---|---|---|
| WO | WO-2007/069078 A2 | 6/2007 |
| WO | WO-2008/004900 A1 | 1/2008 |
| WO | WO-2008/013548 A2 | 1/2008 |
| WO | WO-2011/155852 A1 | 12/2011 |
| WO | WO-2012/047120 A1 | 4/2012 |
| WO | WO-2012/053912 A1 | 4/2012 |
| WO | WO-2012/071983 A1 | 6/2012 |

OTHER PUBLICATIONS

Bumbak et al., Best practices in heterotrophic high-cell density microalgal processes:; Achievements, potential and possible limitations. *Appl. Microbiol. Biotech.* 91:31-46 (2001).

Droop, The nutrient status of algal cells in continuous culture. *J. Marine Biol. Assoc. U.K.* 54(4):825-55 (1974).

Dunstan et al., Essential polyunsaturated fatty acids from 14 species of diatom. (*Bacillariophyceae*) *Phytochemistry* 35: 155-61 (1993).

Ethier et al., Continuous culture of the microalgae Schizochytrium limacinum on biodieselderived crude glycerol for producing docosahexaenoic acid. *Bioresource Technology* 102: 88-93 (2011).

Ganuza et al., Lipid accumulation in Schizochytrium G13/2S produced in continuous culture. *Appl. Microbiol. Biotechnol.* 76:985-90 (2007).

Gill et al., Lipid accumulation in an oleaginous yeast (Candida 107) growing on glucose in singlestage continuous culture. *App. Env. Microbiol.* 33:231-9 (1977).

Hall et al., Lipid accumulation in an oleaginous yeast (Candida 107) growing on glucose under; various conditions in a one- and two-stage continuous culture. *App. Env. Microbiol.* 33:577-84 (1977).

Kendrick et al., Lipid formation in the oleaginous mould Entomophthora exitalis grown in; continuous culture: effects of growth rate, temperature and dissolved oxygen tension on; polyunsaturated fatty acids. *Appl. Microbiol. Biotechnol.* 37:18-22 (1992).

Laing, Cultivation of murine, unicellular algae, Ministry of Agriculture, Fisheries and Food; Directorate of Fisheries Research, *Laboratory Leaflet No.* 67:1-31 (1991).

Lebeau et al., Diatom cultivation and biotechnologically relevant products. Part II: Current and putative products. *App. Microbiol. Biotech.* 60: 624-32 (2003).

Papanikolaou et al., Lipid production by Yarrowia lipolytica growing on industrial glycerol in a single-stage continuous culture. *Bioresouce Technology* 82:43-9 (2002).

Pleisner et al., «http://www.marbio.sdu.dk/uploads/MarBioShell/Pleissner%20-%20VejleNuthetalPoster.pdf», accessed Feb. 8, 2013.

Richardson et al., Effects of nitrogen limitation on the growth and composition of unicellular algae in continuous culture. *Appl. Microbiol.* 18:245-50 (1969).

Wen et al., A perfusion-cell bleeding culture strategy for enhancing the productivity of; eicosapentaenoic acid by Nitzschia laevis. *Appl. Microbiol. Biotechnol.* 57:316-22 (2001).

Wen et al., Continuous cultivation of the diatom Nitzschia laevis for eicospentaenoic acid; production: Physiological study and process optimization. *Biotechnol. Prog.* 18:21-8 (2002).

Wen et al., Perfusion culture of the diatom Nitzschia laevis for ultra-high yield of eicosapentaenoic acid. *Proc. Biochem.* 38:523-9 (2002).

Ykema et al., Optimization of lipid production in the oleaginous yeast Apiotrichum curvatum in wheypermeate. *Appl. Microbiol. Biotechnol.* 29:211-8 (1988).

Zou et al., Production of cell mass and eicosapentaenoic acid (EPA) in ultrahigh cell density; cultures of *Nannochloropsis* sp. (Eustigmatophyceae). *Eur. J. Phycol.* 35(2): 127-33 (2000).

METHODS FOR THE PRODUCTION OF DIATOM BIOMASS

FIELD OF INVENTION

The invention relates to methods of producing a diatom biomass. More particularly, the invention relates to methods to produce a diatom biomass using a continuous culture. In a preferred embodiment the biomass comprises highly unsaturated fatty acid.

BACKGROUND

Diatoms are a widespread group of microalgae and can be found in the oceans, freshwater, and in soils. Biomass from diatom culture (whether naturally or commercially produced) contains a number of products of commercial interest including lipids, fatty acids (particularly highly unsaturated fatty acids—HUFAs), amino acids, pigments and complex natural products of pharmacological interest. The biomass itself also has dietary application (particularly in aquaculture), and the treatment of water contaminated by phosphorus and nitrogen in aquaculture effluent, or heavy metal (bioremediation). A further application in development is the use of silicon derived from frustules (the cell wall or external layer of diatoms) in nanotechnology. However, the commercial relevance of products from diatoms will depend on the cost of their production.

Industrial fermentation is a costly process in terms of capital equipment, nutrients, and energy, and is generally only justified when a relatively high value product is being produced in large quantities.

Different modes of culturing or fermentation are possible. The simplest mode of fermentation and the one that is almost exclusively used in industrial processes is batch fermentation. In batch fermentation, cells are inoculated in nutrient medium, grown for a period of time and then harvested. Fed-batch fermentation is similar to batch but differs in that concentrated nutrients are supplied to the culture during the growth period. Continuous fermentation involves the continuous harvest of culture comprising biomass and a nutrient solution from the fermentation vessel and its replacement with fresh nutrient solution. The rate of harvest in continuous fermentation is chosen so that the density of the cells in culture remains constant. Semi-continuous fermentation is similar to continuous fermentation except that harvests are periodic rather than continuous. Perfusion fermentation involves the continuous harvest of a culture medium which contains the product of interest, while the cells producing the product are retained in the culture.

Where the product of interest is produced within the cells, the cells are generally cultivated to the highest biomass densities possible to get the most efficient volumetric productivity (i.e., amount of product produced per volume of fermentation medium per unit time), thereby minimizing the cost of production of the product of interest. However, at high biomass densities there can be difficulties in providing sufficient oxygen, nutrients and, where applicable, light. For example, in a batch or fed batch fermentation, microbial cultures are generally in a stationary phase at the point of harvest. It is usual for the medium or feeding regime in these types of fermentations to result in the culture being severely limited for one or more nutrients, often as a means of inducing the formation of secondary metabolites (which are often the products of commercial interest).

It was previously known that photosynthetic organisms (e.g., microalgae) can be grown phototrophically under continuous or semi-continuous culture conditions. Under these conditions light is used as the energy source, rather than reduced carbon. Many authors (e.g. Richardson et al. (1969) Applied Microbiology 18:245-250; Droop (1974) J. Mar. Biol. Ass. U.K. 54:825-855; Laing (1991) Lab. Leafl. MAFF Direct. Fish. Res., Lowestoft, (67) 31 pp) have disclosed means of growing algae in continuous or semi-continuous phototrophic culture (turbidostats). In such cultures, cells are generally limited by the amount of light that is available and so culture densities are low and thus volumetric productivity is very low. Advances in photobioreactor technology have overcome the light limitation problem to a certain extent by narrowing the optical plane and allowing cultures to reach higher biomass concentrations (Zou et al. (2000) Eur. J. Phycol. 35:127-133). However, this requires an increase in surface area to volume ratio of the culture and significantly increases the capital cost structure of the reactors. Furthermore, at these concentrations growth is slow (light limited) and thus volumetric productivity is again low. These photobioreactor systems also have the disadvantage that they would be uneconomic to construct for volumes large enough to supply industrial demand and even the best commercially scalable photobioreactor designs still produce biomass densities only about one-tenth that capable in a fermentor. Such photobioreactors are therefore generally considered to be just a laboratory tool for study of the growth of photosynthetic organisms.

Pharmaceuticals, medical foods and nutritional supplement containing highly unsaturated fatty acids (HUFAs) are currently used to treat hundreds of thousands, and potentially will soon be used to treat, millions of patients. Eicosapentaenoic acid (EPA) is a HUFA used as an active metabolite in drug substances. Docosahexaenoic acid (DHA) also has great potential for use in the pharmaceutical, medical food and nutritional supplement industry. An example of their use is the treatment or prophylactic treatment of cardiovascular disease.

HUFAs cannot be chemically synthesized de novo economically, therefore must be extracted from a biological source. Pharmaceutical manufacturers currently rely on fish as the source of HUFAs for production of drug substances. Exclusive reliance on fish oil for such purposes, however, carries a number of serious risks to pharmaceutical manufacturers and drug companies as well as potentially to patients receiving such medications. Such risks include, but are not limited to, those associated with potential supply shortages, which may be financially devastating to drug companies as well as negatively affect patients who rely on medications for their well-being. Fish oil itself is not a specific reference material since its composition differs dramatically between different fish species. Even within a single fish species the composition varies from location to location and it even varies at different times of the year at a single location. Such variability in starting material makes manufacturing a final pharmaceutical product very difficult. Furthermore there is a growing concern over the toxic pollutants such as poly chlorinated biphenyls (PCBs), dioxin, and methyl mercury that are showing up in fish oils. There are also widespread concerns over the long term sustainability of wild fish stocks and aquaculture.

There is an acute need therefore, for alternative sources of HUFAs to fish oil which are consistent, reliable and therefore amenable to commercial and sustainable production methods. Industrial fermentation is one possible alternative for commercial production of HUFAs. However, there are a number of problems with using industrial fermentation on a commercial scale.

A number of authors have disclosed continuous culture of microorganisms for the production of lipids (for example Hall and Ratledge (1977) App. Env. Microbiol 33:577-584; Gill et al. (1977) App. Env. Microbiol. 33231-239; Ykema et al. (1988) Appl. Microbiol. Biotechnol. 29:211-218; Brown et al. (1989) J. Ferm. Bioeng. 68:344-352; Kendrick and Ratledge (1992) Appl. Microbiol. Biotechnol. 37:18-22; Papanikolaou and Aggelis (2002) Bioresouce Technology 82:43-49). Whilst some of these do disclose high volumetric biomass productivity, none of the organisms disclosed produce any highly unsaturated fatty acids (HUFAs; fatty acids with 20 or more carbons and 4 or more double bonds).

Other types of organisms, in particular microalgae of the genus *Crypthecodinium* and marine fungi in the family Thraustochytriales (including *Schizochytrium* species, *Thraustochytrium* species and *Ulkenia* species) may be more uniquely suited to production of HUFAs, and particularly the omega-3 DHA. Whilst these organisms produce the greatest amounts of DHA under conditions of nitrogen limitation and are thus well suited to the fed batch cultures used in industrial processes, some authors have disclosed a continuous heterotrophic culture of these species for the production of DHA. However, most of these continuous cultures were only demonstrated in the laboratory and were at low production rates, which are not commercially viable.

Ganuza and Izquierdo ((2007) Appl. Microbiol. Biotechnol. 76:985-990) disclose continuous culture of *Schizochytrium* G13/2S for the production of DHA. Their maximum biomass productivity occurred at a dilution of 0.04 per hour and a dry weight of 7.7 g/L giving a volumetric productivity of only 7.4 g/L/day.

Ethier et al. ((2011) Bioresource Technology 102:88-93) disclose continuous culture of *Schizochytrium limacinum* for producing DHA. Their highest biomass productivity was only 3.88 g/L/day.

Pleisner and Errikson (http://www.marbio.sdu.dk/uploads/MarBioShell/Pleissner%20-%20VejleNuthetalPoster-.pdf accessed 8 Feb. 2013), disclose continuous culture of *Crypthecodinium cohnii* for producing DHA, but only achieve a biomass productivity of 12 g/L/day. Further, at this volumetric productivity the HUFA content of the biomass was only 1.67%, making the final extraction and processing problematic.

In contrast, Wümpelmann in WO2005/021735 discloses continuous culture of *Schizochytrium limnaceum* for the production of DHA at high culture densities and through this achieves biomass productivities in excess of 100 g/L/day. The author discloses methods that are particularly suitable to producing DHA from this organism, indicating for instance that dissolved oxygen tension should be maintained at low levels, but does not provide sufficient guidance about whether such conditions can even be used for other types of microorganisms or, if so, how such conditions should be varied to allow these sorts of productivities for other organisms with completely different environmental and nutritional requirements. The methods disclosed by the author are also not well suited for production at an industrially relevant scale. Indeed, the examples disclosed are only carried out in 2 L fermenters in the laboratory and the cost of using just one of the media constituents (e.g., casamino acids) as a nitrogen source would be prohibitively expensive at scales of 100 L or more.

Other types of organisms, in particular the diatoms, may be more suited for the production of the omega-3 EPA, especially where it is advantageous for the EPA to be produced with relatively low amounts of DHA present.

Wen and Chen disclose the heterotrophic culture of the diatom *Nitzschia laevis* for the production of the omega-3 fatty acid EPA. However, in true continuous cultures their maximal biomass productivity was only 2.8 g/L/day ((2002) Biotechnol. Prog. 18:21-28), whilst with the addition of perfusion (wherein cells and media are separated, cells are returned to the fermenter and additional fresh media is added), this was raised to 6.75 g/L/day ((2001) Appl Microbiol Biotechnol 57:316-322).

Griffiths et al. (WO2011/155852) disclosed the heterotrophic culture of the diatom *Nitzschia laevis* both in perfusion-aided continuous culture and in true continuous culture. Whilst the authors do no not disclose the volumetric productivities of the cultures, culture dry weights were around 10 g/L or lower and in perfusion-aided continuous culture the total volume removed from the culture was one fermenter volume per day. Even if all this volume were harvest and none were perfusion, the maximum biomass productivity would be significantly higher than described by Wen and Chen, but would still only be around 10 g/L/day.

SUMMARY OF THE INVENTION

According to a first aspect of the invention, there is provided a method of producing a diatom biomass, the method comprising the step of continuously culturing a diatom in a culture medium to produce a volumetric production rate of biomass of at least 20 g dry weight/L/day, wherein the culture medium is designed to provide the essential nutrients to maintain the diatom in log phase growth.

Preferably the diatom produces at least one highly unsaturated fatty acid (HUFA).

Preferably the HUFA is selected from any one or more of EPA, DHA and ARA.

Preferably the HUFA is an omega-3 fatty acid.

Preferably the diatom biomass contains a total HUFA level of at least 2% of dry cell weight of the biomass. Preferably the diatom biomass contains a total HUFA level of at least 3% of dry cell weight of the biomass.

Preferably the diatom biomass contains a mixture of EPA and DHA at a level of at least 2% dry cell weight of the biomass.

Preferably the diatom biomass contains at least one HUFA at a level of at least 2% of dry cell weight of the biomass.

Preferably the diatom biomass contains EPA at a level of at least 2% of dry cell weight of the biomass.

Preferably the volumetric production rate of biomass is at least 25 g dry weight/L/day. Preferably the volumetric production rate of biomass is at least 30 g dry weight/L/day.

Preferably the mean volumetric production rate of biomass is at least 20 g dry weight/L/day over a period of at least 72 hours. Preferably the mean volumetric production rate of biomass is at least 20 g dry weight/L/day over a period of at least a week. Preferably the mean volumetric production rate of biomass is at least 20 g dry weight/L/day over a period of at least a month. Preferably the mean volumetric production rate of biomass is at least 20 g dry weight/L/day over a period of at least 2 months.

Preferably the method does not include a perfusion culture of the cultured diatoms.

Preferably the diatom is a *Nitzschia* species. Preferably the diatom is *Nitzschia laevis*. Preferably the diatom is *Nitzschia laevis* strain In1CS20.

Preferably the diatom is a *Cyclotella* species.

Preferably the diatom is a *Phaeodactylum* species.

Preferably, the diatom is cultivated heterotrophically.

Preferably the culture medium comprises a reduced carbon source.

Preferably the reduced carbon source is selected from any one or more of: glucose, fructose, high fructose corn syrup, monosaccharides, disaccharides, alcohols, acetic acid or its salts.

Preferably a source of silicate is added continuously during the course of the culture.

Preferably the source of silicate is an alkali metal silicate.

Preferably the alkali metal silicate is sodium silicate or potassium silicate.

Preferably the sodium silicate is added continuously at a level of between 20 and 120 mg sodium metasilicate pentahydrate for every gram dry cell weight of biomass produced in the culture.

Preferably the silicate is added at between 40 and 100 mg sodium metasilicate pentahydrate per gram of dry cell weight of biomass produced. Preferably the silicate is added at 75 mg sodium metasilicate pentahydrate per gram of dry cell weight of biomass produced.

Preferably the culture pH is maintained within the range 7.0 to 9.0. Preferably the culture pH is maintained within the range 7.5 to 8.5. Preferably the culture pH is maintained within the range 8.0 to 8.5.

Preferably the culture is maintained at a temperature of between 15 and 30° C. Preferably the culture is maintained at a temperature of between 20 and 25° C.

Preferably agitation and/or back pressure are provided to maintain a dissolved oxygen level at or above 10% of air saturation.

Preferably the dissolved oxygen level is maintained at or above 20% of air saturation. Preferably the dissolved oxygen level is maintained at or above 30% of air saturation. Preferably the dissolved oxygen level is maintained at or above 40% of air saturation.

Preferably the method includes replacement of at least 50% of the culture volume with fresh medium every 24 hours.

Preferably the method includes replacement of at least 10% of the culture volume with fresh medium every 4 hours.

Preferably the method includes replacement of at least 5% of the culture volume with fresh medium every 2 hours.

Preferably the method includes replacement of at least 0.2% of the culture volume with fresh medium every 5 minutes.

Preferably the method includes at least 500 liters of culture medium.

Preferably the method further includes separating the biomass from the culture and concentrating the biomass to produce a biomass concentrate.

Preferably the biomass is concentrated by any one or more of: centrifugation, flocculation, filtration, or floatation.

Preferably the biomass is concentrated by continuous centrifugation.

Preferably the method further includes the step of drying of the biomass concentrate.

Preferably the biomass concentrate is dried by any one or more of: spray drying, freeze drying, tunnel drying, vacuum drying, drum drying.

According to a second aspect of the invention, there is provided a method of producing a diatom biomass, the method comprising:
  a. cultivating a diatom in a culture medium to produce an active culture;
  b. removing a portion of the active culture to collect the biomass;
  c. adding fresh culture medium to the remaining active culture that is substantially equivalent in volume to the portion of the active culture removed in step (b) and further cultivating the diatom; and
  d. repeating step (b) and step (c) as desired so that at least 20 g dry cell weight of biomass per liter of active culture is collected in a 24 hour period,
  wherein the culture medium is designed to provide the essential nutrients to maintain the diatom in log phase growth.

Preferably, the addition of fresh culture medium in step (c) is done in one portion.

Alternatively, the addition of fresh culture in step (c) is done in multiple portions that total to a substantially equivalent volume to the portion removed in step (b).

Preferably the diatom produces at least one highly unsaturated fatty acid (HUFA).

Preferably the HUFA is selected from any one or more of EPA, DHA and ARA.

Preferably the HUFA is an omega-3 fatty acid.

Preferably the diatom biomass contains a total HUFA level of at least 2% of dry cell weight of the biomass. Preferably the diatom biomass contains a total HUFA level of at least 3% of dry cell weight of the biomass.

Preferably the diatom biomass contains a mixture of EPA and DHA at a level of at least 2% dry cell weight of the biomass.

Preferably the diatom biomass contains at least one HUFA at a level of at least 2% of dry cell weight of the biomass.

Preferably the diatom biomass contains EPA at a level of at least 2% of dry cell weight of the biomass.

Preferably step (b) and step (c) are repeated so that at least 25 g dry cell weight of biomass per liter of active culture is collected in a 24 hour period. Preferably step (b) and step (c) are repeated so that at least 30 g dry cell weight of biomass per liter of active culture is collected in a 24 hour period.

Preferably at least 20 g dry cell weight of biomass is collected per liter of active culture each day for at least three consecutive days. Preferably at least 20 g dry cell weight of biomass is collected per liter of active culture each day for at least seven consecutive days. Preferably at least 20 g dry cell weight of biomass is collected per liter of active culture each day for at least thirty consecutive days. Preferably at least 20 g dry cell weight of biomass is collected per liter of active culture each day for at least sixty consecutive days.

Preferably steps (b) and (c) are repeated at least 5 times. Preferably steps (b) and (c) are repeated at least 20 times. Preferably steps (b) and (c) are repeated at least 100 times.

Preferably the density of biomass in the active culture is at least 20 g/L. Preferably the density of biomass in the active culture is at least 30 g/L.

Preferably the method does not include perfusion of the active culture.

Preferably the diatom is a *Nitzschia* species. Preferably the diatom is *Nitzschia laevis*. Preferably the diatom is *Nitzschia laevis* strain In1CS20.

Preferably the diatom is a *Cyclotella* species.

Preferably the diatom is a *Phaeodactylum* species.

Preferably, the diatom is cultivated heterotrophically.

Preferably the culture medium comprises a reduced carbon source.

Preferably the reduced carbon source is selected from any one or more of: glucose, fructose, high fructose corn syrup, monosaccharides, disaccharides, alcohols, acetic acid or its salts.

Preferably, a source of silicate is added continuously during the course of the culture.

Preferably the source of silicate is an alkali metal silicate. Preferably the alkali metal silicate is sodium silicate or potassium silicate.

Preferably the sodium silicate is added continuously at a level of between 20 and 120 mg sodium metasilicate pentahydrate for every gram dry cell weight of biomass produced in the culture.

Preferably the silicate is added at between 40 and 100 mg sodium metasilicate pentahydrate per gram of dry cell weight of biomass produced. Preferably the silicate is added at 75 mg sodium metasilicate pentahydrate per gram of dry cell weight of biomass produced.

Preferably the culture pH is maintained within the range 7.0 to 9.0. More preferably the culture pH is maintained within the range 7.5 to 8.5. Most preferably the culture pH is maintained within the range 8.0 to 8.5.

Preferably the culture is maintained at a temperature of between 15 and 30° C. More preferably the culture is maintained at a temperature of between 20 and 25° C.

Preferably agitation and/or back pressure are provided to maintain a dissolved oxygen level at or above 10% of air saturation.

Preferably the dissolved oxygen level is maintained at or above 20% of air saturation. Preferably the dissolved oxygen level is maintained at or above 30% of air saturation. Preferably the dissolved oxygen level is maintained at or above 40% of air saturation.

Preferably steps (b) and (c) are carried out sequentially.

Alternatively steps (b) and (c) are carried out simultaneously.

Preferably the method includes the removing of a portion of the active culture in step (b) and the adding of fresh culture medium in step (c) such that there is replacement of at least 50% of the active culture volume every 24 hours.

Preferably the method includes the removing of a portion of the active culture in step (b) and the adding of fresh culture medium in step (c) such that there is replacement of at least 10% of the active culture volume every 4 hours.

Preferably the method includes the removing of a portion of the active culture in step (b) and the adding of fresh culture medium in step (c) such that there is replacement of at least 5% of the active culture volume every 2 hours.

Preferably the method includes removing a portion of the active culture in step (b) and the adding of fresh culture medium in step (c) continuously at a rate of at least 0.2% of the active culture volume every 5 minutes.

Preferably step (a) includes at least 500 liters of active culture.

Preferably the method further includes concentrating the portion of the active culture removed in step (b), to produce a biomass concentrate.

Preferably the biomass is concentrated by any one or more of: centrifugation, flocculation, filtration, or floatation.

Preferably the biomass is concentrated by continuous centrifugation.

Preferably the method further includes the step of drying of the biomass concentrate.

Preferably the biomass concentrate is dried by any one or more of: spray drying, freeze drying, tunnel drying, vacuum drying, drum drying.

Alternatively the portion of the active culture removed in step (b) may be dried directly by any one or more of: spray drying, freeze drying, tunnel drying, vacuum drying, drum drying.

According to a third aspect of the invention, there is provided an active culture in a continuous culture, the active culture comprising culture medium, a diatom at a diatom biomass density of at least 20 g/L.

Preferably the density of biomass is at least 30 g/L.

Preferably, the diatom produces at least one highly unsaturated fatty acid (HUFA).

Preferably the HUFA is selected from any one or more of EPA, DHA and ARA.

Preferably the HUFA is an omega-3 fatty acid.

Preferably the diatom biomass contains a total HUFA level of at least 2% of dry cell weight of the biomass. Preferably the diatom biomass contains a total HUFA level of at least 3% of dry cell weight of the biomass.

Preferably the diatom biomass contains a mixture of EPA and DHA at a level of at least 2% dry cell weight of the biomass.

Preferably the diatom biomass contains at least one HUFA at a level of at least 2% of dry cell weight of the biomass.

Preferably the diatom biomass contains EPA at a level of at least 2% of dry cell weight of the biomass.

Preferably the diatom is selected from *Nitzschia* species, *Cyclotella* species, *Phaeodactylum* species.

Preferably the diatom is *Nitzschia laevis*. Preferably the diatom is *Nitzschia laevis* strain In1CS20.

According to the fourth aspect of the invention there is provided a diatom biomass produced by the method of first or second aspects of the invention.

According to the fifth aspect of the invention there is provided a composition of a highly unsaturated fatty acid or an ester thereof obtained from the biomass produced by the methods of the first or second aspects of the invention.

According to a sixth aspect of the invention there is provided a method of producing a composition of a highly unsaturated fatty acid (HUFA) or an ester thereof, the method including the step of extracting the HUFA or an ester thereof from the biomass produced by the methods of the first or second aspects of the invention.

Preferably the HUFA is in its native form, being a triglyceride, phospholipid, or glycolipid.

Preferably the HUFA in its native form is extracted from the biomass using a polar solvent.

Alternatively the HUFA in its native form is extracted from the biomass using a nonpolar solvent.

Alternatively the HUFA in its native form is extracted from the biomass using a solvent composition comprising a combination of polar and nonpolar solvents.

Preferably the polar solvent is selected from any one or more of an alcohol, acetone, and polar supercritical fluids.

Preferably the non-polar solvent is selected from any one or more of hexane, isohexane, triglycerides, and nonpolar supercritical fluids.

Preferably the extracted HUFA in its native form is subsequently esterified in the presence of ethanol to form a fatty acid ethyl ester (FAEE) of the HUFA.

Preferably the FAEE of the HUFA is purified by any one or a combination of chromatography, solvent partitioning, short path distillation, molecular distillation, and High-performance liquid chromatography (HPLC).

Preferably the HUFA in its native form is saponified to produce a free fatty acid of the HUFA.

Preferably the HUFA in its free fatty acid form are purified by chromatography, molecular distillation and/or HPLC.

Alternatively the HUFA in its native form is purified by chromatography.

According to an seventh aspect of the invention there is provided a nutritional supplement for humans and/or animals comprising the biomass of the third or fourth aspects of the invention.

According to an eighth aspect of the invention there is provided a nutritional supplement for humans and/or animals comprising the biomass produced by the first or second aspects of the invention.

According to a ninth aspect of the invention there is provided a nutritional supplement, medical food, food or feed additive or pharmaceutical product comprising the composition produced by the method of the sixth aspect of the invention.

Further aspects of the invention, which should be considered in all its novel aspects, will become apparent to those skilled in the art upon reading of the following description which provides at least one example of a practical application of the invention.

BRIEF DESCRIPTION OF THE DRAWINGS

Embodiments of the invention will now be described, by way of example only, with reference to the accompanying drawings in which.

DETAILED DESCRIPTION OF PREFERRED EMBODIMENTS

In general terms, the invention relates to methods of culturing a diatom to produce diatom biomass at commercially useful production rates.

Diatom biomass contains a number of products of commercial interest including lipids, fatty acids, amino acids, pigments and complex natural products of pharmacological interest. The biomass itself also has commercial use.

The production of highly unsaturated fatty acid (HUFA) is of particular interest, particularly the production of the HUFA eicosapentaenoic acid (EPA). It has been found that diatoms can be induced to produce EPA in the absence of high levels of co-concentrating compounds such as DHA, which allows for the production of EPA that is capable of being further concentrated/purified.

It was previously thought that production of biomass by microbes could only be economic if the microbes were grown under batch or fed batch fermentation conditions where the maximum density of microbial biomass is reached. In particular, it was also believed that some classes of microbes, such as diatoms, could not even be used for economic production of biomass under batch or fed-batch fermentation conditions because the cultures suffer from slow growth and/or they have a relatively low proportion of their biomass as the desired commercial product, or their unique nutritional requirements make them very difficult to grow. Diatoms have particular and unusual environmental and nutritional needs, including a requirement for large amounts of silica (a structural element of their cell walls) and, for the most part, a requirement for a saline growth medium. Whilst these fermentative microbes can be grown in fed-batch mode in classical fermenters in the laboratory, the characteristics of the organisms result in such a low volumetric productivity that the cost of industrial scale fermentation becomes prohibitive.

The phases of microbial growth are broadly classified as lag phase (where the microbes are adapting themselves to the growth conditions), log phase (also referred to as logarithmic phase or exponential phase, where the microbes are multiplying at an exponential rate), stationary phase (where the maximum cell density is reached as growth rate and death rate are equal; this is often due to a growth limiting factor such as deletion of nutrients) and death phase (where the death rate is higher than the growth rate).

Surprisingly, the inventors have found it possible to achieve volumetric productivities sufficiently high to become economic through the use of continuous culture of diatoms. By maintaining the culture in, or close to, log-phase growth these diatoms may have a lower biomass density and/or content of the desired molecules at the time of harvest compared to conventional stationary phase culture produced by batch and fed-batch fermentations, but the overall productivity of the culture was found to be far higher than can be achieved in batch or fed-batch culture. Further, the productivity of desired HUFA was found to be higher. Typically, the transfer into stationary phase of a culture results in the induction of the production of large amounts of commercially useful products and the transfer into stationary phase of a microbial culture is typically initiated by some form of nutrient limitation, typically nitrogen limitation. The inventors, however, surprisingly found that with diatoms, particularly diatoms which can be grown heterotrophically, this is often not the case and nutrient limitation can result in the production of undesired molecules rather than the products for which the culture is being grown. The inventors surprisingly attained a much higher volumetric productivity of biomass and certain desired products, such as HUFAs, when the nutrients were not limited and the culture was maintained in a logarithmic phase of growth.

Continuous culture is where fresh culture medium is continuously added, while the active culture that is maintained in log phase growth is continuously removed to keep the culture volume constant. Semi-continuous culture is where a volume of the active culture (i.e. cells activity growing in log phase in a culture medium) is removed at regular or at least periodic time intervals and an equal or substantially similar volume (i.e. approximately equivalent) of fresh medium is added back to the culture to replace that which has been removed such that the average volume of the active culture remains substantially constant over the time of the culture. For a semi-continuous culture it is usual to first remove a portion of the active culture prior to replacing the volume with fresh culture medium, since this sequence of events does not require additional space in the fermentor vessel. However, it is possible to reverse the sequence of events if there are particular commercial benefits for doing so. For the avoidance of doubt unless the context clearly requires otherwise, throughout the description and the claims, reference to "continuous culture" or "continuously culturing or the like" should be taken to include both continuous culture and semi-continuous culture.

A person skilled in the art would be aware that the culture medium will require nutrients to allow and sustain the growth of the microbe. The culture medium will comprises a nitrogen source, (for example but not limited to ammonium ion, nitrate, yeast extract, soy flour, peptone, tryptone), a phosphate source and a sulfur source. However, for growth of diatoms the culture medium also needs to contain a source of silica, since silica is the basis of the cell walls of all diatoms. The culture medium additionally contains one or more of: magnesium, calcium, cobalt, manganese, boron, zinc, molybdenum, iron, chromium, nickel, selenium, copper and vitamins. It will be apparent to a person skilled in the art that the nutrients in the culture medium of diatoms will be significantly different from those of other microorganisms. However, when provided with the teaching in the present application a person skilled in the art would either be aware of or would be able to use experimentation to determine the components required in the culture medium that would not limit the growth of diatoms.

However, surprisingly, the inventors have found that there are key differences in the way in which a medium needs to be designed to support continuous culture. Traditionally, limitation in a single nutrient can be used to determine how much of this particular nutrient is required to make a certain dry weight of biomass. For continuous culture, however, the inventors have found that the medium is preferably designed so that the active culture remains in log-phase. The inventors have found that this results in higher nutrient requirements on a per gram dry cell weight basis. In the methods of the invention, the culture medium preferably is designed to provide all the essential nutrients in quantities to maintain the diatoms at, or near log phase growth.

Surprisingly, the inventors have found it is not sufficient to simply take processes that operate at low culture densities and scale the concentration of nutrients in the culture medium to make more biomass; particularly careful attention must be given to culture medium design. The inventors have found that at low culture densities, imbalances in nutrients are relatively unimportant since the concentrations of compounds are generally low. However, for fast, continuous growth at high biomass density (as shown in the present invention), nutrient provision must be closely matched to the needs of the organism while growing in the logarithmic phase. To achieve high culture densities, relatively high concentrations of nutrients are required, but the inventors have also found that nutrients provided in excess to diatoms can also accumulate over time to levels at which they alter biomass composition and/or inhibit growth rate. Certain cellular requirements such as zinc or copper can actually be toxic to the diatoms when provided in too high a concentration. Addition of copper salts, for example, is a well-established method of killing diatoms and preventing their regrowth in ponds, lagoons and pools. Diatoms appear to be unexpectedly susceptible to overprovision of a number of nutrients that have toxic effects at high concentration.

Nutrients that are under-provided become depleted over the course of several consecutive harvests, again resulting in undesirable changes in biomass composition or alterations in growth. The inventors have found that whilst in certain circumstances, slight limitations of one or more nutrients may be desirable, for example if it results in a greater proportion of HUFA in the biomass, in general the reduction of growth rate (i.e., transfer into a stationary phase) is undesirable. As a result, the inventors have found that there must be particular attention paid to elements of the medium such as trace metals and phosphate for which the diatoms may have significant internal stores, since depletion of these will occur over a longer time frame.

Even if one has achieved the correct nutrient balance at one particular level of biomass productivity, one cannot simply double the level of all ingredients in the medium and expect double the level of biomass productivity. Addition of some ingredients, such as a reduced carbon source, may be directly related to the amount of biomass that is produced, but can also have an inhibitory effect on growth at higher concentrations. As a result, feeding strategies need to be evolved to ameliorate this fundamental problem. For example, it may be preferable to provide replacement culture medium for diatoms in discrete portions over time rather than replace the whole volume of harvest at one time. Some ingredients such as sodium chloride, for example, are present for the osmotic balance of the medium and are therefore not provided directly in proportion to the biomass produced. Some nutrients, such as zinc, must be maintained within a certain range of concentrations. Too low and growth rates drop, too high and toxic effects cause reduced growth and eventually culture death. Some nutrients, such as potassium, play dual roles and so a balance has to be made between, for example, their osmotic effect, and use as a nutrient. While the quantities of nutrients in the culture will be dependent on the microbe used and the volume of culture, after being provided with the insight and teaching in the present application that it is desirous to maintain diatom cells in log phase growth in continuous culture, and that this requires a different media composition than is required for normal fermentations, a person skilled in the art would be able to use routine experimentation to determine the quantities of components required in the culture medium to maintain the diatom at, or near log phase growth. For example, the inventors have shown in Example 8 an example of a procedure to determine the quantity of sulfur required for maintaining an active, log-phase growth of a diatom.

Of particular issue when dealing with culture of diatoms is the provision of silicate. Even at relatively modest concentrations, the inventors have found that silicate can interact with other medium ingredients to form precipitates and gels, removing both itself and other nutrients from solution and making them unavailable for use by the diatoms. As the amount of biomass being produced increases, special attention needs to be paid to the addition of the silicate (which is provided proportionally to the biomass to be produced), to prevent this from occurring. The silicate is preferably added continuously during the course of the culture to aid in the reduction of silicate precipitates forming, and to aid in providing a quantity of silicate to maintain the culture at, or near log phase growth, (for example a method of addition of silicate is described in WO2012/053912). The source of silicate is preferably an alkali metal silicate, for example (but not limited to) sodium silicate or potassium silicate. In preferred embodiments, sodium silicate is added continuously at a level of between 20 and 120 mg sodium metasilicate pentahydrate for every gram dry cell weight of biomass produced in the culture, more preferably between 40 and 100 mg sodium metasilicate pentahydrate per gram of dry cell weight of biomass produced, and most preferably 75 mg sodium metasilicate pentahydrate for every gram dry cell weight of biomass produced in the culture.

The inventors have found that it is possible to continuously culture diatoms at high densities, in the region of 20 g Dry Cell Weight (DCW)/L or higher, for example 20 to 150 g DCW/L, or more preferably 30 to 100 g DCW/L, even more preferably 30 to 70 g DCW/L. Preferably the dry cell weight of the culture at the time of harvest remains within +/−5% of the mean of harvests during the time over which the culture runs in order to maintain a high density of diatoms in the culture. Such densities of diatoms in the continuous culture of the invention allow for high volumetric production rates of at least 20 grams DCW of biomass per liter of active culture per day (DCW/L/day) (i.e. 20 grams of biomass produced per liter of active culture in the fermentation vessel per day), more preferably at least 30 grams DCW of biomass per liter of active culture per day, but may be optimized using the teaching of the present application to be as high as 50 g DCW/L/day of biomass, more preferably 60 g DCW/L/day of biomass, even more preferably 70 g DCW/L/day of biomass or higher. The range of the production rates is therefore any one of the preferred minimum values to any one of the preferred maximum values, for example (but not limited to), 20 to 50 g DCW/L/day of biomass, more preferably 20 to 60 g DCW/L/day of biomass, more preferably 20 to 70 g DCW/L/day of biomass.

The continuous cultures of the methods of the invention preferably include replacement of at least 35% by volume of the active culture every 24 hours, more preferably at least 40% by volume, more preferably at least 50% by volume, even more preferably at least 60% by volume. The methods alternatively include replacement of at least 6% by volume of the active culture every 4 hours, more preferably at least 8% by volume, more preferably at least 10% by volume, more preferably at least 12% by volume most preferably at least 15% by volume. In a further alternative the methods of the invention preferably include replacement of at least 3% by volume of the active culture every 2 hours, more preferably at least 4% by volume, more preferable at least 6% by volume, most preferably at least 7% by volume. In yet a further alternative, the methods of the invention preferably include replacement of at least 0.15% by volume of the active culture every 5 minutes, more preferably 0.2% by volume, more preferably at least 0.3%, most preferably at least 0.35% by volume. The volume of harvest and replacement should be chosen to match the growth rate of the organism in log phase so that the culture density in sequential harvests does not drop and the culture does not enter stationary phase. Whilst semi-continuous harvest every 24, 4, and 2 hours and continuous harvest are provided by way of examples, any interval of less than 24 hours that allows the cells to remain in logarithmic growth may be used so that the interval between harvests can be chosen to suit the needs of downstream processing although it is noted that, for a given dry weight at harvest and growth rate, more frequent harvests provide a higher biomass productivity.

In some cases, previous culture methods have used perfusion to increase the density and productivity of cultures of microbes. Perfusion is where cells and medium from active culture are separated, cells are returned to the fermenter and additional fresh medium is added. The methods of the present invention preferably do not include perfusion of the active culture, as this procedure adds further costs and procedures which would be impractical on an industrial scale for biomass production. Perfusion cultures are also extremely susceptible to contamination and require extraordinary measures to maintain axenic cultures for long periods of time. The maintenance of sterility is important since invading contaminant organisms that grow faster than the production organism can quickly come to dominate the culture over the course of several harvests at which point the culture must be abandoned. The methods of the invention surprisingly provide high productivity culture, without the need for perfusion. While the inventors have found care should be taken to keep contaminants out of the fermenter during the methods of the invention particularly at both the harvest of culture and refill of fresh medium, this problem is lessened by the lack of need for perfusion.

The inventors have shown that the methods of the invention can be carried out at scales of at least 12 liters of active culture, more preferably at least 14 liters of active culture, more preferably at least 400 liters of active culture, even more preferably at least 500 liters of active culture. However, once provided with the teaching in the present application larger scale cultures such as at least 10,000 liters, at least 100,000 liters, and even at least 200,000 liters can be used for industrial production.

To be commercially viable, the continuous cultures of the invention are preferably sustainable over a period of time. The inventors have demonstrated the methods of the invention can be maintained for at least 72 hours (3 days), more preferably at least 5 days, even more preferably a week (7 days), even more preferably at least a month (30 days), most preferably at least 2 months (60 days). For a semi-continuous culture the cycle of removal of a portion of active culture and the replacement of fresh culture medium is preferably repeated at least 5 times. However, in the examples of the invention provided in the present application (see Examples 1-5), the cultures were discontinued after 60 days (after the removal of active culture and replacement with fresh medium well over 100 times) without any indication that the cultures could not be maintained longer. Thus, there is no indication the cultures could not be continued for periods of months or years without issue. In a preferred embodiment the average volumetric production rate of biomass is at least 20 g dry weight/L/day over a period of at least 72 hours (3 days), more preferably at least a week (7 days), more preferably at least a month (30 days), even more preferably at least 2 months (60 days).

Preferably the methods of the invention comprise cultivating an identified diatom. Preferably the strain of diatom is selected, when under culture conditions, for a capability to produce at least one HUFA, preferably EPA and/or DHA. A person skilled in the art will be aware of diatom species that are capable of producing HUFA, or would be able to carry out routine experimentation in order to determine this (for example, see Dunstan et al. (1993) Phytochemistry 35:155-161). In preferred embodiments, the diatom is selected from, but not limited to, a *Nitzschia* species, a *Cyclotella* species or a *Phaeodactylum* species. Most preferably the diatom is *Nitzschia laevis,* for example (but not limited to) *Nitzschia laevis* strain In1CS20.

A person skilled in the art would be aware of methods to "seed" the fermentation with the required microbe. The fermentation will generally be carried out in a fermentation vessel, or other suitable container as would be apparent to a person skilled in the art.

The diatom biomass produced by the methods of the present invention is in a metabolic state (log-growth phase) that is quite different in composition from stationary phase cultures. When diatoms which are capable of producing highly unsaturated fatty acids (HUFA) are used, these conditions result in relatively high levels of one or more HUFA. Most preferably the HUFA is EPA, but it may also beneficially be a mixture of more than one HUFA, preferably EPA, DHA and ARA, more preferably EPA and DHA. Both EPA and DHA are omega-3 fatty acids and are known to have particularly beneficial health properties. These fatty acids, or their esterified forms, can be used as pharmaceuticals, medical foods, food or feed additives, cosmetic products, or nutritional supplements. ARA is an omega-6 fatty acid and is also known to have beneficial health properties. Preferably the diatom biomass contains a total HUFA level (which can be made up of a mixture of different HUFA) of at least 2% of dry cell weight of the biomass, more preferably at least 3% of dry cell weight of the biomass. More preferably the diatom biomass contains a mixture of EPA and DHA at a level of at least 2% dry cell weight of the biomass, even more preferably at least 3% of dry cell weight of the biomass. At least one HUFA is preferably produced by the methods of the invention at a level of at least 2% of dry cell weight of the biomass (i.e. a single HUFA at a level of 2%), more preferably at least 2.5% of dry cell weight of the biomass, more preferably at least 2.7% of dry cell weight of the biomass, even more preferably at least 3.2% of dry cell weight of the biomass. The HUFA produced is most preferably EPA. The maximum level of total HUFA or single HUFA in the biomass will be dependent on the fine tuning of conditions and the choice of diatom, once a person skilled in the art is provided with the teaching in the specification. However, the inventors believe that the maximum limit is likely to be in the region of 5%, more preferably 10%, more preferably 15%, even more preferably 20% of dry cell weight. The range of the content of one or more HUFA in the biomass is therefore any one of the preferred minimum values to anyone of the preferred maximum values, for example (but not limited to), the level of HUFA is preferably 1 to 20% of dry cell weight of the biomass, more preferably 2 to 15% of dry cell weight of the biomass, more preferably 2 to 10% of dry cell weight of the biomass, more preferably 2.7 to 10% of dry cell weight of the biomass, even more preferably 3.2 to 10% of dry cell weight of the biomass.

Current art teaches that most microalgae must be cultured photosynthetically to produce HUFA. In a particularly preferred aspect of the invention, the inventors have surprisingly found that diatoms are able to be cultured heterotrophically using continuous fermentation to produce HUFA at a high productivity. This allows for commercial production without the need to provide light for the high density fermentation, thus overcoming the engineering issues associated with providing sufficient light to high density cultures previously discussed. Where the diatoms are cultivated heterotrophically, a reduced carbon source is preferably provided in the culture medium. Preferably the reduced carbon source is selected from (but not limited to) any one or more of: glucose, fructose, high fructose corn syrup, monosaccharides, disaccharides, alcohols, acetic acid or its salts.

Current art teaches that, to gain high volumetric productivity of HUFAs, batch or fed-batch conditions should be used where cells are taken into stationary phase in which a state of oleogenesis is induced, usually through the use of nitrogen and/or phosphate limitation and the composition of the algal biomass is thereby significantly different from compositions of biomass growing in log-phase. In a particularly preferred aspect of the invention, the inventors have surprisingly determined that diatoms can be cultured heterotrophically using continuous fermentation of the diatom maintained in log-phase to produce HUFA at high volumetric productivity. This allows for commercial production of organisms, such as diatoms, which are unsuited to batch or fed-batch fermentation, thus overcoming the issues with growing them at scale.

The inventors have also found the culture pH is preferably maintained within the range 7.0 to 9.0, more preferably within the range 7.5 to 8.5, most preferably within the range 8.0 to 8.5. The temperature of the culture is preferably maintained between 15 and 30° C., more preferably at a temperature of between 20 and 25° C. Preferably agitation and/or back pressure are provided to maintain a dissolved oxygen level at or above 10%, more preferably 20%, even more preferably 30% of air saturation. The dissolved oxygen level is even more preferably maintained at or above 40% of air saturation. Such conditions promote growth of the diatom and HUFA formation (when a diatom capable of producing HUFA is used). The dissolved oxygen levels are preferably maintained for at least 80%, more preferably 90% of the cultivation time. Brief drops below the preferred dissolved oxygen levels are considered within the scope of the present invention as they should not significantly affect the culture.

The invention also includes the active culture (i.e. diatom cells activity growing in log phase in a culture medium) in the continuous culture which, prior to separation of the biomass, extraction or purification steps, will include the culture medium, diatoms at a biomass density of at least 20 g/L. Preferably, where a diatom capable of producing HUFA is used, the diatom biomass contains a highly unsaturated fatty acid (HUFA).

Following separation of portions of the active culture from the continuous culture, the diatom biomass component is preferably concentrated to substantially remove or separate the liquid component to produce a biomass concentrate, for example by centrifugation or continuous centrifugation or other means known in the art for harvesting biomass, for example but not limited to centrifugation, flocculation, filtration and/or floatation. The cells of the biomass can also optionally be washed to remove excess medium and/or killed by heat treatment (e.g., pasteurization) or otherwise (for example to denature endogenous enzymes which may decrease product yield). The biomass is optionally dried to reduce or eliminate water, for example by spray drying, freeze drying, tunnel drying, vacuum drying and/or drum drying. The dried biomass is optionally milled to form a fine powder, or optionally formed into pellets. Alternatively the portion of active culture removed from the continuous culture may be dried directly without pre-concentration.

The diatom biomass of the invention may be subjected to one or more extraction steps to extract desired products, for example HUFA or esters thereof, from the biomass to yield a composition (for example a HUFA composition). Suitable extraction techniques are well known in the art and will be dependent on the desired product. For example to extract a HUFA, the biomass may be extracted with a non-selective lipid solvent (e.g. near critical di-methyl ether or ethanol) and recovered from the solvent as a residue. Alternatively, the biomass may be extracted using other polar or nonpolar solvents including, but not limited to hexane, alcohol, acetone, supercritical or liquid carbon dioxide, or mixtures thereof (for example hexane and isopropanol). The biomass may be extracted with solvent either in a batch or a counter-current fashion. The solvent (containing the HUFA) is separated from the extracted biomass, for example by (but not limited to) settling, filtration, centrifugation. The HUFA (or ester thereof) are recovered from the solvent.

The HUFA present in the biomass are in the form of free fatty acids and/or esterified forms of the fatty acid. Examples of esterified forms of the fatty acid include triglycerides, phospholipids, and glycolipids (collectively referred to as lipids). The lipids are the native form of the HUFA, (i.e. the form naturally found in the biomass before any external chemical modification). The free fatty acids are either cleaved from the lipids while still in the biomass (for example by the action of enzymes), or can optionally by cleaved from the lipids (for example to form an alternative ester, or to the free fatty acid) during the extraction, enriching and/or purification steps.

Following extraction, the further step of enriching HUFA or purifying one or more HUFA from the mixture may be performed using techniques well known in the art. For example, the extracted material may be treated with acids, alkalis and/or enzymes in the presence of alcohol or water to form free fatty acids or fatty acid alkyl esters. For example, the HUFA may be transesterified to form the fatty acid ethyl ester (FAEE). The ester may optionally be purified in order to achieve a required standard of purity. Examples of purification processes include chromatography, molecular distillation and/or high-performance liquid chromatography (HPLC). For the avoidance of doubt HPLC is sometimes referred to as high-pressure liquid chromatography. Alternatively the lipids in the biomass are saponified to form the free fatty acids. The free fatty acids are optionally purified or separated, for example, by (but not limited to) chromatography. The HUFA, purified in the free fatty acid form, may then be used as such or converted into an ethyl ester (FAEE) using processes well known in the art.

Following purification of the HUFA, or ester thereof, the HUFA can then be used for various food or feed applications suitable for human and/or animal consumption including, but not limited to, pharmaceutical products, medical foods, food additives, cosmetic products, dietary supplements, or feed additives. In some cases the biomass itself can be used for various food or feed applications including, but not limited to, pharmaceutical products, medical foods, food additives, cosmetic products, dietary supplements, or feed additives.

By using the methods of the invention to provide controlled cultivation of a diatom, a HUFA product can be provided in a consistent, sustainable and traceable form (i.e., by good manufacturing processes) without the concern for environmental pollutants, all of which plague fish oil as a source for similar HUFA products.

Definitions and Abbreviations

Highly unsaturated fatty acid (HUFA) is a fatty acid containing 20 carbons or more, with 4 or more double bonds. They may be omega-3 or omega-6.

Fatty acids are described in the form CX:Y, wherein the number X describes the number of carbon atoms and the number Y describes the number of double bonds in the fatty acid. Where Y equals zero the fatty acid is described as saturated, where Y is greater than zero the fatty acid is described as unsaturated. The position and type of the double bonds may be specified as, for example, "cis 5, 11, 14" where the numbers reflect the location of the carbon-carbon double bonds, counting from the carboxylic acid end of the molecule.

Unless the context clearly requires otherwise, throughout the description and the claims, reference to "fatty acid" should be taken to include both the free fatty acids and esterified forms of the fatty acid which are suitable for human use (e.g., for consumption or topical applications), Examples of esterified forms of the fatty acid which are suitable for human consumption include triglycerides, phospholipids, glycolipids, and ethyl esters. Methyl esters are unfavorable in compositions for human consumption because they release methanol into the body during processing in the human gut and they are therefore are not preferred within the compositions and methods for production. A term such as C20:5, for example, is understood to include both the free fatty acid and esterified forms of the fatty acid (not including methyl esters) with the number of carbon atoms and double bonds referring solely to the fatty acid portion of the ester.

Omega-3 fatty acid is a fatty acid with the first double bond three carbon atoms from the methyl end (the omega end) of the molecule. Omega-3 is often shortened to n-3 and both terms are herein used interchangeably.

Omega-6 fatty acid is a fatty acid with the first double bond six carbon atoms from the methyl end of the molecule. Omega-6 is often shortened to n-6.

EPA, C20:5 n-3, Eicosapentaenoic acid, is an omega-3 fatty acid with twenty carbon atoms and five double bonds.

ARA, 020:4 n-6, Arachidonic acid, is an omega-6 fatty acid with twenty carbon atoms and four double bonds.

DHA, C22:6 n-3, Docosahexaenoic acid, is an omega-3 fatty acid with twenty-two carbon atoms and six double bonds.

DCW, dry cell weight, means the weight of a biomass once all water has been removed.

Log phase or logarithmic growth is used synonymously with exponential growth throughout this description and all are used consistently with definitions well known in the art.

Heterotrophic culture means a culture of organisms for which at least 90% of the energy supply for the culture is derived from supplied nutrients which are usually a form or forms of organic carbon (e.g. glucose, acetate). Therefore a maximum of 10% of the energy supply may be derived from light energy. Preferably, less than 5% or more preferably less than 1% of the energy supply is derived from light energy. More preferably, the whole of the energy supply is from supplied nutrients.

Active culture means a biomass of cells activity growing in log phase in a culture medium contained in a suitable vessel, for example a fermenter.

Photoautotrophic culture (or photoautotroph microbes or diatoms) means a culture of organisms for which the sole energy source is light.

Nutrient limitation means that the absence or low level of the nutrient in question causes the organism to undergo metabolic changes that would not occur if the nutrient were present at higher levels and is essentially the entrance into the stationary phase of a culture. A culture would be considered to be in a non-limiting nutrient condition if growth proceeds in a logarithmic fashion.

Unless the context clearly requires otherwise, throughout the description and the claims, reference to "continuous culture" or "continuously culturing" should be taken to include both strict continuous culture (where fresh culture medium is continuously added, while active culture is continuously removed to keep the culture volume constant) and semi-continuous culture (where a volume of active culture is removed at regular or at least periodic time intervals and an equal or substantially similar volume of fresh medium is added to the culture to replace that which has been removed such that the average volume of active culture remains substantially constant over the time of the culture). For a semi-continuous culture it is usual to first remove a portion of the active culture prior to replacing the volume with fresh culture medium, since this sequence of events does not require additional space in the fermentor vessel. However, it is possible to reverse the sequence of events.

Unless the context clearly requires otherwise, throughout the description and the claims, reference to "diatoms" or "diatom" should be taken to include all organisms of the class Bacillariophyceae including but not limited to pennate (e.g., *Nitzschia*) and centric (e.g., *Cyclotella*) diatoms.

Unless the context clearly requires otherwise, throughout the description and the claims, the words "comprise", "comprising", and the like, are to be construed in an inclusive sense as opposed to an exclusive or exhaustive sense, that is to say, in the sense of "including, but not limited to".

It is intended that reference to a range of numbers disclosed herein (for example, 1 to 10) also incorporates reference to all rational numbers within that range (for example, 1, 1.1, 2, 3, 3.9, 4, 5, 6, 6.5, 7, 8, 9 and 10) and also any range of rational numbers within that range (for example, 2 to 8, 1.5 to 5.5 and 3.1 to 4.7).

EXAMPLES

Example 1

Semi-continuous Culture of *Nitzschia laevis*

A culture of *Nitzschia laevis* strain In1CS20 was grown in 14 L culture in a 20 L stirred vessel. The pH was maintained at 8.0 or above by the addition of NaOH, temperature was maintained at 20° C., and pressure maintained at around 500 mbar above surroundings. Agitation was provided to keep dissolved oxygen above 40% saturation.

The cells were grown up to a density of around 40 g dry cell weight per liter of culture and harvest initiated. Every 4 hours, 1.4 liters of culture was withdrawn from the vessel as harvest, and the volume was made back up to 14 L with hourly feeds of approximately 400 mL fresh medium. This was sustained for 7 days.

The fresh medium was composed of:

|  | g/L |
| --- | --- |
| Glucose monohydrate | 95 |
| Sodium Nitrate NaNO$_3$ | 10.1 |
| Yeast Extract | 3.1 |
| Na$_2$HPO$_4$ | 1.16 |
| Sodium chloride NaCl | 8.4 |
| Potassium chloride KCl | 1.17 |
| Magnesium sulfate heptahydrate MgSO$_4$·7H$_2$O | 4.9 |
| Calcium chloride dihydrate CaCl$_2$·2H$_2$O | 0.204 |
| Sodium sulphate | 0.586 |

|  | mg/L |
| --- | --- |
| Cobalt chloride hexahydrate CoCl$_2$·6H$_2$O | 0.081 |
| Manganese chloride 4-hydrate MnCl$_2$·4H$_2$O | 0.843 |
| Boric acid H$_3$BO$_3$ | 103.1 |
| Zinc chloride ZnCl$_2$ | 1.05 |
| Sodium molybdate dihydrate Na$_2$MoO$_4$·2H$_2$O | 1.363 |
| Ferric chloride hexahydrate | 7.22 |
| Citrate | 675 |
| Copper sulfate | 0.024 |
| Vitamin B12 | 202.7 |
| Thiamine | 0.34 |
| Biotin | 0.34 |

In addition to the hourly feeds, sodium metasilicate was also provided to the culture as a separate, near continuous, feed such that it was provided at around 7.5% w/w sodium metasilicate (pentahydrate)/dry cell weight.

Optical density of the culture was recorded every 10 minutes and remained within a range +/−2% of the average throughout the 7 day period. The culture dry cell weight (DCW) was measured from an additional 100 mL sample taken at the time of harvest one on four of the seven days. This sample was also used for composition analysis.

The dry cell weight measurements were then used to calculate the DCW at each of the other harvests.

By multiplying the volume of harvest by the DCW, a biomass collection and thus a biomass productivity were calculated.

In the Table 1 below DCW and EPA content of biomass figures in italics are calculated from the surrounding data.

TABLE 1

| Day 1 | DCW (g/L) | Harvest (L) | Biomass Collected (g) |
| --- | --- | --- | --- |
| Harvest 1 | 42.0 | 1.5 | 63.0 |
| Harvest 2 | *41.6* | 1.4 | 58.2 |
| Harvest 3 | *41.4* | 1.4 | 58.0 |
| Harvest 4 | *41.3* | 1.4 | 57.9 |
| Harvest 5 | *41.2* | 1.4 | 57.7 |
| Harvest 6 | *41.1* | 1.4 | 57.6 |
| Biomass Productivity (g/L/day) | | 25.2 | |
| EPA Content of Biomass (%) | | 2.5 | |
| EPA Productivity (mg/L/h) | | 26.2 | |

| Day 2 | DCW (g/L) | Harvest (L) | Biomass Collected (g) |
| --- | --- | --- | --- |
| Harvest 1 | 41.0 | 1.4 | 57.4 |
| Harvest 2 | *40.8* | 1.4 | 57.2 |
| Harvest 3 | *40.7* | 1.4 | 56.9 |
| Harvest 4 | *40.5* | 1.4 | 56.7 |
| Harvest 5 | *40.3* | 1.4 | 56.5 |
| Harvest 6 | *40.2* | 1.4 | 56.2 |
| Biomass Productivity (g/L/day) | | 24.3 | |
| EPA Content of Biomass (%) | | 2.5 | |
| EPA Productivity (mg/L/h) | | 25.4 | |

| Day 3 | DCW (g/L) | Harvest (L) | Biomass Collected (g) |
| --- | --- | --- | --- |
| Harvest 1 | 40.0 | 1.5 | 60.0 |
| Harvest 2 | *39.7* | 1.4 | 55.5 |
| Harvest 3 | *39.6* | 1.4 | 55.5 |
| Harvest 4 | *39.6* | 1.4 | 55.4 |
| Harvest 5 | *39.6* | 1.4 | 55.4 |
| Harvest 6 | *39.5* | 1.4 | 55.3 |
| Biomass Productivity (g/L/day) | | 24.1 | |
| EPA Content of Biomass (%) | | 2.5 | |
| EPA Productivity (mg/L/h) | | 25.1 | |

| Day 4 | DCW (g/L) | Harvest (L) | Biomass Collected (g) |
| --- | --- | --- | --- |
| Harvest 1 | 39.5 | 1.5 | 59.3 |
| Harvest 2 | *39.3* | 1.4 | 55.1 |
| Harvest 3 | *39.5* | 1.4 | 55.3 |
| Harvest 4 | *39.6* | 1.4 | 55.5 |
| Harvest 5 | *39.8* | 1.4 | 55.7 |
| Harvest 6 | *39.9* | 1.4 | 55.9 |
| Biomass Productivity (g/L/day) | | 24.1 | |
| EPA Content of Biomass (%) | | 2.5 | |
| EPA Productivity (mg/L/h) | | 25.1 | |

| Day 5 | DCW (g/L) | Harvest (L) | Biomass Collected (g) |
| --- | --- | --- | --- |
| Harvest 1 | *40.1* | 1.4 | 56.1 |
| Harvest 2 | *40.3* | 1.4 | 56.4 |
| Harvest 3 | *40.5* | 1.4 | 56.7 |
| Harvest 4 | *40.7* | 1.4 | 57.0 |
| Harvest 5 | *40.9* | 1.4 | 57.3 |
| Harvest 6 | *41.1* | 1.4 | 57.5 |
| Biomass Productivity (g/L/day) | | 24.4 | |
| EPA Content of Biomass (%) | | 2.5 | |
| EPA Productivity (mg/L/h) | | 25.4 | |

TABLE 1-continued

Day 6

| | DCW (g/L) | Harvest (L) | Biomass Collected (g) |
|---|---|---|---|
| Harvest 1 | 41.3 | 1.4 | 57.8 |
| Harvest 2 | 41.5 | 1.4 | 58.1 |
| Harvest 3 | 41.7 | 1.4 | 58.3 |
| Harvest 4 | 41.8 | 1.4 | 58.6 |
| Harvest 5 | 42.0 | 1.4 | 58.8 |
| Harvest 6 | 42.2 | 1.4 | 59.1 |
| Biomass Productivity (g/L/day) | | 25.1 | |
| EPA Content of Biomass (%) | | 2.5 | |
| EPA Productivity (mg/L/h) | | 26.1 | |

Day 7

| | DCW (g/L) | Harvest (L) | Biomass Collected (g) |
|---|---|---|---|
| Harvest 1 | 42.4 | 1.5 | 63.6 |
| Harvest 2 | 41.9 | 1.4 | 58.7 |
| Harvest 3 | 41.8 | 1.4 | 58.5 |
| Harvest 4 | 41.7 | 1.4 | 58.4 |
| Harvest 5 | 41.6 | 1.4 | 58.2 |
| Harvest 6 | 41.4 | 1.4 | 58.0 |
| Biomass Productivity (g/L/day) | | 25.4 | |
| EPA Content of Biomass (%) | | 2.5 | |
| EPA Productivity (mg/L/h) | | 26.4 | |

Example 2

The culture of Example 1 was reset by harvesting 50% of the volume and allowing growth back to a density of around 40 g dry cell weight per liter of culture before harvest was again initiated.

For this example harvests of between 0.7 and 0.8 L were carried out every two hours (harvest volume being adjusted to keep the dry weight at harvest close to constant). The volume was then made back up to 14 L with two refills; one of approximately 400 mL fresh medium immediately following harvest and one providing the remaining volume to reach 14 L an hour later. Medium composition was as for Example 1. Silicate was fed to the culture in the same manner as was used in Example 1.

The optical density of the culture was recorded every 10 minutes and remained within a range of +/−2% of the average throughout the 7 day period. An additional 100 mL sample was taken for determination of culture dry cell weight and biomass composition at the time of harvest on six of the eight days.

Biomass Productivity was calculated as per Example 1. In the Table 2 below DCW and EPA content of biomass figures in italics were calculated from the surrounding data.

TABLE 2

Day 1

| | DCW (g/L) | Harvest (L) | Biomass Collected (g) |
|---|---|---|---|
| Harvest 1 | 40.0 | 0.8 | 32.0 |
| Harvest 2 | *39.7* | 0.7 | 27.8 |
| Harvest 3 | *39.7* | 0.7 | 27.8 |
| Harvest 4 | *39.7* | 0.7 | 27.8 |
| Harvest 5 | *39.7* | 0.7 | 27.8 |
| Harvest 6 | *39.7* | 0.7 | 27.8 |
| Harvest 7 | *39.7* | 0.7 | 27.8 |
| Harvest 8 | *39.8* | 0.7 | 27.8 |
| Harvest 9 | *39.8* | 0.7 | 27.8 |
| Harvest 10 | *39.8* | 0.7 | 27.8 |
| Harvest 11 | *39.8* | 0.7 | 27.8 |
| Harvest 12 | *39.8* | 0.7 | 27.9 |
| Biomass Productivity (g/L/day) | | 24.1 | |
| EPA Content of Biomass (%) | | 2.6 | |
| EPA Productivity (mg/L/h) | | 26.2 | |

Day 2

| | DCW (g/L) | Harvest (L) | Biomass Collected (g) |
|---|---|---|---|
| Harvest 1 | 39.8 | 0.9 | 35.8 |
| Harvest 2 | *39.4* | 0.8 | 31.6 |
| Harvest 3 | *39.4* | 0.8 | 31.5 |
| Harvest 4 | *39.3* | 0.8 | 31.5 |
| Harvest 5 | *39.3* | 0.8 | 31.4 |
| Harvest 6 | *39.2* | 0.8 | 31.4 |
| Harvest 7 | *39.1* | 0.8 | 31.3 |
| Harvest 8 | *39.1* | 0.8 | 31.3 |
| Harvest 9 | *39.0* | 0.8 | 31.2 |
| Harvest 10 | *39.0* | 0.8 | 31.2 |
| Harvest 11 | *38.9* | 0.8 | 31.1 |
| Harvest 12 | *38.9* | 0.8 | 31.1 |
| Biomass Productivity (g/L/day) | | 27.2 | |
| EPA Content of Biomass (%) | | 2.5 | |
| EPA Productivity (mg/L/h) | | 28.3 | |

Day 3

| | DCW (g/L) | Harvest (L) | Biomass Collected (g) |
|---|---|---|---|
| Harvest 1 | 38.8 | 0.9 | 34.9 |
| Harvest 2 | *38.5* | 0.8 | 30.8 |
| Harvest 3 | *38.5* | 0.8 | 30.8 |
| Harvest 4 | *38.6* | 0.8 | 30.8 |
| Harvest 5 | *38.6* | 0.8 | 30.9 |
| Harvest 6 | *38.6* | 0.8 | 30.9 |
| Harvest 7 | *38.6* | 0.8 | 30.9 |
| Harvest 8 | *38.6* | 0.8 | 30.9 |
| Harvest 9 | *38.6* | 0.8 | 30.9 |
| Harvest 10 | *38.7* | 0.8 | 30.9 |
| Harvest 11 | *38.7* | 0.8 | 30.9 |
| Harvest 12 | *38.7* | 0.8 | 30.9 |
| Biomass Productivity (g/L/day) | | 26.8 | |
| EPA Content of Biomass (%) | | 2.6 | |
| EPA Productivity (mg/L/h) | | 29.0 | |

Day 4

| | DCW (g/L) | Harvest (L) | Biomass Collected (g) |
|---|---|---|---|
| Harvest 1 | *38.7* | 0.8 | 31.0 |
| Harvest 2 | *38.7* | 0.8 | 31.0 |
| Harvest 3 | *38.7* | 0.8 | 31.0 |
| Harvest 4 | *38.8* | 0.8 | 31.0 |
| Harvest 5 | *38.8* | 0.8 | 31.0 |
| Harvest 6 | *38.8* | 0.8 | 31.1 |
| Harvest 7 | *38.8* | 0.8 | 31.1 |
| Harvest 8 | *38.9* | 0.8 | 31.1 |
| Harvest 9 | *38.9* | 0.8 | 31.1 |
| Harvest 10 | *38.9* | 0.8 | 31.1 |
| Harvest 11 | *38.9* | 0.8 | 31.2 |
| Harvest 12 | *39.0* | 0.8 | 31.2 |
| Biomass Productivity (g/L/day) | | 26.6 | |
| EPA Content of Biomass (%) | | 2.5 | |
| EPA Productivity (mg/L/h) | | 27.7 | |

Day 5

| | DCW (g/L) | Harvest (L) | Biomass Collected (g) |
|---|---|---|---|
| Harvest 1 | *39.0* | 0.8 | 31.2 |
| Harvest 2 | *39.0* | 0.8 | 31.2 |
| Harvest 3 | *39.0* | 0.8 | 31.2 |
| Harvest 4 | *39.0* | 0.8 | 31.2 |
| Harvest 5 | *39.1* | 0.8 | 31.3 |

TABLE 2-continued

| | | | |
|---|---|---|---|
| Harvest 6 | 39.1 | 0.8 | 31.3 |
| Harvest 7 | 39.1 | 0.8 | 31.3 |
| Harvest 8 | 39.1 | 0.8 | 31.3 |
| Harvest 9 | 39.1 | 0.8 | 31.3 |
| Harvest 10 | 39.1 | 0.8 | 31.3 |
| Harvest 11 | 39.2 | 0.8 | 31.3 |
| Harvest 12 | 39.2 | 0.8 | 31.3 |
| Biomass Productivity (g/L/day) | | 26.8 | |
| EPA Content of Biomass (%) | | 2.4 | |
| EPA Productivity (mg/L/h) | | 26.8 | |

Day 6

| | DCW (g/L) | Harvest (L) | Biomass Collected (g) |
|---|---|---|---|
| Harvest 1 | 39.2 | 0.9 | 35.3 |
| Harvest 2 | 39.0 | 0.8 | 31.2 |
| Harvest 3 | 39.2 | 0.8 | 31.3 |
| Harvest 4 | 39.3 | 0.8 | 31.5 |
| Harvest 5 | 39.5 | 0.8 | 31.6 |
| Harvest 6 | 39.6 | 0.8 | 31.7 |
| Harvest 7 | 39.7 | 0.8 | 31.8 |
| Harvest 8 | 39.9 | 0.8 | 31.9 |
| Harvest 9 | 40.0 | 0.8 | 32.0 |
| Harvest 10 | 40.2 | 0.8 | 32.1 |
| Harvest 11 | 40.3 | 0.8 | 32.2 |
| Harvest 12 | 40.5 | 0.8 | 32.4 |
| Biomass Productivity (g/L/day) | | 27.5 | |
| EPA Content of Biomass (%) | | 2.3 | |
| EPA Productivity (mg/L/h) | | 26.4 | |

Day 7

| | DCW (g/L) | Harvest (L) | Biomass Collected (g) |
|---|---|---|---|
| Harvest 1 | 40.6 | 0.85 | 34.5 |
| Harvest 2 | 40.2 | 0.75 | 30.2 |
| Harvest 3 | 40.1 | 0.75 | 30.1 |
| Harvest 4 | 40.0 | 0.75 | 30.0 |
| Harvest 5 | 39.9 | 0.75 | 29.9 |
| Harvest 6 | 39.8 | 0.75 | 29.9 |
| Harvest 7 | 39.7 | 0.75 | 29.8 |
| Harvest 8 | 39.7 | 0.75 | 29.7 |
| Harvest 9 | 39.6 | 0.75 | 29.7 |
| Harvest 10 | 39.5 | 0.75 | 29.6 |
| Harvest 11 | 39.4 | 0.75 | 29.5 |
| Harvest 12 | 39.3 | 0.75 | 29.5 |
| Biomass Productivity (g/L/day) | | 25.9 | |
| EPA Content of Biomass (%) | | 2.4 | |
| EPA Productivity (mg/L/h) | | 25.9 | |

Day 8

| | DCW (g/L) | Harvest (L) | Biomass Collected (g) |
|---|---|---|---|
| Harvest 1 | 39.2 | 0.85 | 33.3 |
| Harvest 2 | 39.1 | 0.75 | 29.3 |
| Harvest 3 | 39.3 | 0.75 | 29.5 |
| Harvest 4 | 39.5 | 0.75 | 29.6 |
| Harvest 5 | 39.7 | 0.75 | 29.8 |
| Harvest 6 | 39.9 | 0.75 | 29.9 |
| Harvest 7 | 40.1 | 0.75 | 30.1 |
| Harvest 8 | 40.3 | 0.75 | 30.3 |
| Harvest 9 | 40.6 | 0.75 | 30.4 |
| Harvest 10 | 40.8 | 0.75 | 30.6 |
| Harvest 11 | 41.0 | 0.75 | 30.7 |
| Harvest 12 | 41.2 | 0.75 | 30.9 |
| Biomass Productivity (g/L/day) | | 26.0 | |
| EPA Content of Biomass (%) | | 2.5 | |
| EPA Productivity (mg/L/h) | | 27.1 | |

Example 3

The culture of Example 2 was switched from a harvest every 2 hours to a harvest once per 24 hours. At the time of harvest, 7 L (50%) of the volume of the culture in the fermenter was removed from the fermenter over the course of 70 minutes. On completion of harvest, refill of the fermenter was started with approximately 400 mL fresh medium being added back to the fermenter every hour until the full volume of 14 L was reached.

Fresh medium and silicate provision were as for the previous examples.

A 100 mL sample was taken at harvest time for determination of culture dry cell weight and composition. Cell dry weights ranged from 40.4 g/L on day 1 to 44.6 g/L on day 5 and 43.9 g/L on day 6 giving biomass productivities of between 20.5 and 22.6 g/L/day.

EPA content of biomass was between 2.5 and 2.7% of dry cell weight.

Example 4

The culture of Example 3 was switched from harvest every 24 hours to a near-continuous culture. Once the culture had reached a dry weight of over 40 g/L, 30 mL of medium was added every 5 minutes. Silicate was also added as per example 1. Harvests were carried out as required to maintain the culture volume between 14.0 and 14.2 L. Including the additional volume added as silicate, and the volume taken as samples approximately 8.9 L of medium was added and harvested per day.

Samples were taken for determining culture dry cell weight and composition at 9 am on weekdays. Biomass productivities were calculated on the basis that an average between two 9 am dry weight measurements would be representative of the 24 hour period. Biomass productivities are shown in Table 3 below.

TABLE 3

| Day | DCW at 9am (g/L) | Average dry weight for calculation (g/L) | Harvest volume (L) | Biomass Production (g/L) | EPA Content (%) | EPA Productivity (mg/L/hour) |
|---|---|---|---|---|---|---|
| 1 | 44.5 | 42.7 | 8.9 | 27.1 | 2.7 | 30.5 |
| 2 | 40.9 | 41.2 | 8.9 | 26.2 | 2.8 | 30.5 |
| 3 | | 41.7 | 8.9 | 26.5 | not measured | |
| 4 | | 42.2 | 8.9 | 26.8 | not measured | |
| 5 | 42.5 | 42.8 | 8.9 | 27.2 | 2.7 | 30.6 |
| 6 | 43.1 | 42.9 | 8.9 | 27.3 | 2.9 | 33.0 |
| 7 | 42.8 | 42.8 | 8.9 | 27.2 | 2.8 | 31.8 |

Example 5

Figure 1:
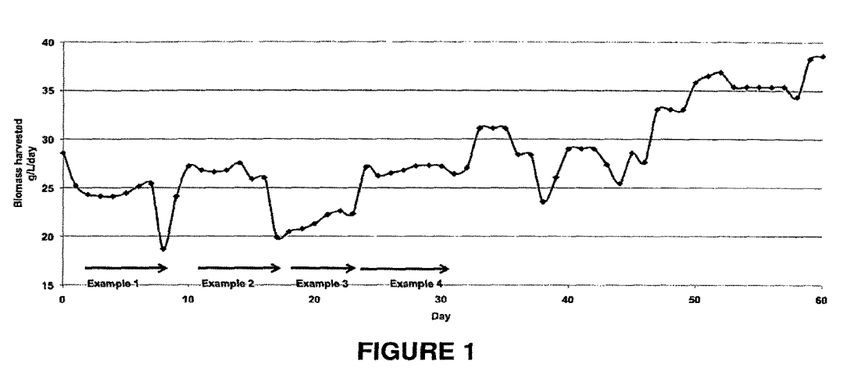
FIG. 1 shows amount of biomass harvested in grams per day per liter of a continuous culture of the invention.

The culture of Example 4 was kept in continuous culture past the seven day period of the example. After being reset with a 7.2 L harvest, it was switched to a 4 hourly harvest regime in which the volume of active culture removed was replaced with fresh culture medium in one addition after harvest concluded. This continued for a further month. With the exception of day 8 of the culture, caused by the reset between Examples 1 and 2, and day 18 of the culture, caused by the reset between examples 2 and 3, the biomass productivity of the culture as measured from 9 am to 9 am did not drop below 20 g/L/day for a period of 60 days as shown in FIG. 1 (note that productivities over weekends after Example 4 are plotted as averages for the weekend). In the later stages of the culture biomass productivities in excess of 35 g/L/day were seen. With EPA at around 2.5% of biomass at this time, this gave EPA productivities of over 35 mg EPA/L/hour. The same medium was used throughout and the increases in productivity are attributed to changes in agitation and pressure to improve oxygen availability.

As well as producing EPA, the organism produced both ARA and DHA. A typical biomass composition included DHA at around 0.15% of biomass and ARA at around 0.1% of biomass.

Example 6

A culture of *Nitzschia laevis* strain In1CS20 was grown in 500 L culture in a 600 L airlift vessel. pH was maintained at 8.0 or above by the addition of NaOH, temperature was maintained at 20° C., and pressure at around 500 mbar above surroundings. Airflow was adjusted to keep the dissolved oxygen levels above 30% saturation at the bottom of the vessel.

The cells were grown up to a density of around 40 g dry cell weight per liter of culture and harvest initiated. Every 4 hours, 40 liters of culture were withdrawn from the vessel as harvest and the volume made back up to 500 L with fresh medium. This was sustained for 6 days. On day 4, the operating volume in the fermenter was reduced to 480 since the airflow had risen to the point where the height of foam in the fermenter was nearing the top plate. The harvest was reduced proportionally to 38 L every 4 hours.

The fresh medium was composed of:

|  | g/L |
| --- | --- |
| Glucose monohydrate | 120 |
| Sodium Nitrate NaNO$_3$ | 12.7 |
| Yeast Extract | 3.9 |
| Na$_2$HPO$_4$ | 1.47 |
| Sodium chloride NaCl | 7.5 |
| Potassium chloride KCl | 1.04 |
| Magnesium sulfate heptahydrate MgSO$_4$•7H$_2$O | 4.4 |
| Calcium chloride dihydrate CaCl$_2$•2H$_2$O | 0.181 |
| Sodium sulphate | 0.521 |

|  | mg/L |
| --- | --- |
| Cobalt chloride hexahydrate CoCl$_2$•6H$_2$O | 0.072 |
| Manganese chloride 4-hydrate MnCl$_2$•4H$_2$O | 0.750 |
| Boric acid H$_3$BO$_3$ | 91.643 |
| Zinc chloride ZnCl$_2$ | 0.936 |
| Sodium molybdate dihydrate Na$_2$MoO$_4$•2H$_2$O | 1.212 |
| Ferric chloride hexahydrate | 6.42 |
| Citrate | 600.0 |
| Copper sulfate | 0.022 |
| Vitamin B12 | 180.2 |
| Thiamine | 0.302 |
| Biotin | 0.302 |

In addition to the media refills, sodium metasilicate was provided to the culture as a separate, near continuous, feed such that it was provided at around 7.5% w/w sodium metasilicate (pentahydrate)/dry cell weight.

The culture dry cell weight was measured at the first harvest and samples taken at these times for composition analysis on days two to six. Biomass productivity was calculated as per Example 1.

The culture dry weight (DCW), biomass productivity, EPA content and EPA productivity are shown in Table 4.

TABLE 4

| Day 1 | DCW (g/L) | Harvest (L) | Biomass Collected (g) |
| --- | --- | --- | --- |
| Harvest 1 | 46.6 | 40.0 | 1864.0 |
| Harvest 2 | 46.6 | 40.0 | 1864.7 |
| Harvest 3 | 46.6 | 40.0 | 1865.3 |
| Harvest 4 | 46.6 | 40.0 | 1866.0 |
| Harvest 5 | 46.7 | 40.0 | 1866.7 |
| Harvest 6 | 46.7 | 40.0 | 1867.3 |
| Biomass Productivity (g/L/day) | | 22.4 | |
| EPA Content of Biomass (%) | | Not measured | |
| EPA Productivity (mg/L/h) | | unknown | |

| Day 2 | DCW (g/L) | Harvest (L) | Biomass Collected (g) |
| --- | --- | --- | --- |
| Harvest 1 | 46.7 | 40.0 | 1868.0 |
| Harvest 2 | 46.8 | 40.0 | 1871.3 |
| Harvest 3 | 46.9 | 40.0 | 1874.6 |
| Harvest 4 | 46.9 | 40.0 | 1878.0 |
| Harvest 5 | 47.0 | 40.0 | 1881.3 |
| Harvest 6 | 47.1 | 40.0 | 1884.7 |
| Biomass Productivity (g/L/day) | | 22.5 | |
| EPA Content of Biomass (%) | | 2.3 | |
| EPA Productivity (mg/L/h) | | 21.6 | |

| Day 3 | DCW (g/L) | Harvest (L) | Biomass Collected (g) |
| --- | --- | --- | --- |
| Harvest 1 | 47.2 | 40.0 | 1888.0 |
| Harvest 2 | 47.6 | 40.0 | 1903.0 |
| Harvest 3 | 48.0 | 40.0 | 1918.2 |
| Harvest 4 | 48.3 | 40.0 | 1933.5 |
| Harvest 5 | 48.7 | 40.0 | 1948.8 |
| Harvest 6 | 49.1 | 40.0 | 1964.4 |
| Biomass Productivity (g/L/day) | | 23.1 | |
| EPA Content of Biomass (%) | | 2.6 | |
| EPA Productivity (mg/L/h) | | 25.0 | |

| Day 4 | DCW (g/L) | Harvest (L) | Biomass Collected (g) |
| --- | --- | --- | --- |
| Harvest 1 | 49.5 | 38.0 | 1881.0 |
| Harvest 2 | 50.3 | 38.0 | 1909.7 |
| Harvest 3 | 51.0 | 38.0 | 1938.7 |
| Harvest 4 | 51.8 | 38.0 | 1968.3 |
| Harvest 5 | 52.6 | 38.0 | 1998.3 |
| Harvest 6 | 53.4 | 38.0 | 2028.7 |
| Biomass Productivity (g/L/day) | | 24.4 | |
| EPA Content of Biomass (%) | | 2.5 | |
| EPA Productivity (mg/L/h) | | 25.4 | |

| Day 5 | DCW (g/L) | Harvest (L) | Biomass Collected (g) |
| --- | --- | --- | --- |
| Harvest 1 | 54.2 | 38.0 | 2059.6 |
| Harvest 2 | 53.6 | 38.0 | 2037.5 |
| Harvest 3 | 53.0 | 38.0 | 2015.6 |
| Harvest 4 | 52.5 | 38.0 | 1994.0 |
| Harvest 5 | 51.9 | 38.0 | 1972.5 |
| Harvest 6 | 51.4 | 38.0 | 1951.4 |
| Biomass Productivity (g/L/day) | | 25.1 | |
| EPA Content of Biomass (%) | | 2.2 | |
| EPA Productivity (mg/L/h) | | 23.0 | |

TABLE 4-continued

|  | Day 6 | | |
| --- | --- | --- | --- |
|  | DCW (g/L) | Harvest (L) | Biomass Collected (g) |
| Harvest 1 | 50.8 | 38.0 | 1930.4 |
| Harvest 2 | 49.9 | 38.0 | 1896.0 |
| Harvest 3 | 49.0 | 38.0 | 1862.1 |
| Harvest 4 | 48.1 | 38.0 | 1828.9 |
| Harvest 5 | 47.3 | 38.0 | 1796.3 |
| Harvest 6 | 46.4 | 38.0 | 1764.3 |
| Biomass Productivity (g/L/day) |  | 23.1 |  |
| EPA Content of Biomass (%) |  | 2.2 |  |
| EPA Productivity (mg/L/h) |  | 21.2 |  |

Example 7

Instructions for Larger Scale Culture

A culture of *Nitzschia laevis* strain In1CS20 is grown in 70,000 L of media in a 80,000 L stirred tank fermenter. pH is maintained at 8.0 or above by the addition of KOH, temperature is maintained at 20° C., and pressure at around 300 mbar above surroundings. Agitation is adjusted to keep the dissolved oxygen levels above 30% saturation at the 60,000 L point in the vessel.

The cells are grown up to a density of around 40 g dry cell weight per liter of culture and harvest initiated. Every 4 hours, around 7000 liters of culture are withdrawn from the vessel as harvest using pressure as a motive force and the volume made back up to 70,000 L with fresh medium. This is sustained for 21 days and produces the equivalent of around 35 tons dry weight of algal biomass or 24 g/L/day over the course of the period.

In addition to the media refills, sodium metasilicate solution is provided to the culture as a separate, continuous, feed such that it is provided at around 7.5% w/w sodium metasilicate (pentahydrate)/dry cell weight.

Example 8

Ascertaining Nutrient (Sulfur) Levels to Support Log Phase Growth of the Diatom

Fully defined growth medium lacking sulfur was made up in which all nutrients apart from sulfur were supplied in non-limiting amounts at pH 8.0.

A series of duplicate sterile 250 mL Ehrlenmeyer flasks were prepared by adding 100 mL of the sulfur-free medium to which varying amounts of magnesium sulfate had been added. The upper concentration of sulfur was chosen to represent an expected slight excess requirement of the cells with other concentrations representing 40%, 30%, 20%, 10% and 0% of this level.

The flasks were then inoculated with a low level of exponentially growing *Nitzschia laevis* cells (5 mg dry weight per flask) to limit carry-over of sulfur from the previous culture. The flasks were placed on an orbital shaker at 20° C. to grow.

Culture dry weights were determined on days 3 to 8 of the culture. Aside from the culture with no added sulfur, similar levels of growth were seen up to day 4 of the culture, at which point cell densities diverged with those cultures receiving more sulfur growing to higher densities. (See FIG. 2).

Figure 3:
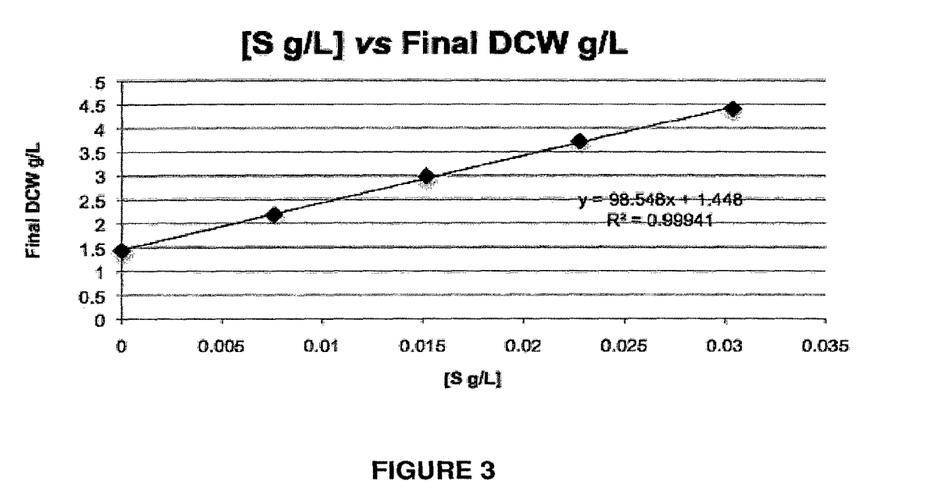
FIG. 3 shows graph of culture dry weights achieved against sulfur provision.

By plotting peak dry cell weight against sulfur provision (FIG. 3), it was determined that the inoculum provided sufficient sulfur to allow biomass to accumulate to around 1.5 g/L but thereafter approximately a maximum of around 98.5 mg of dry cell weight could be produced per mg of sulfur. This allowed the determination of the minimum amount of sulfur required to support growth of biomass in a traditional batch fermentation (10.1 mg S per g dry cell weight).

Figure 2:
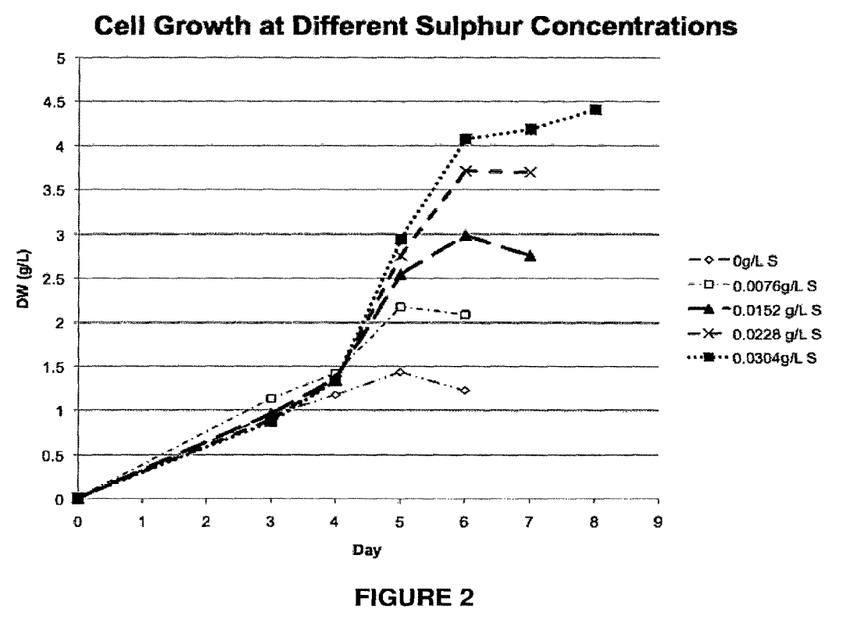
FIG. 2 shows culture dry weights over time for cultures with different provisions of sulfur.
Figure 4:
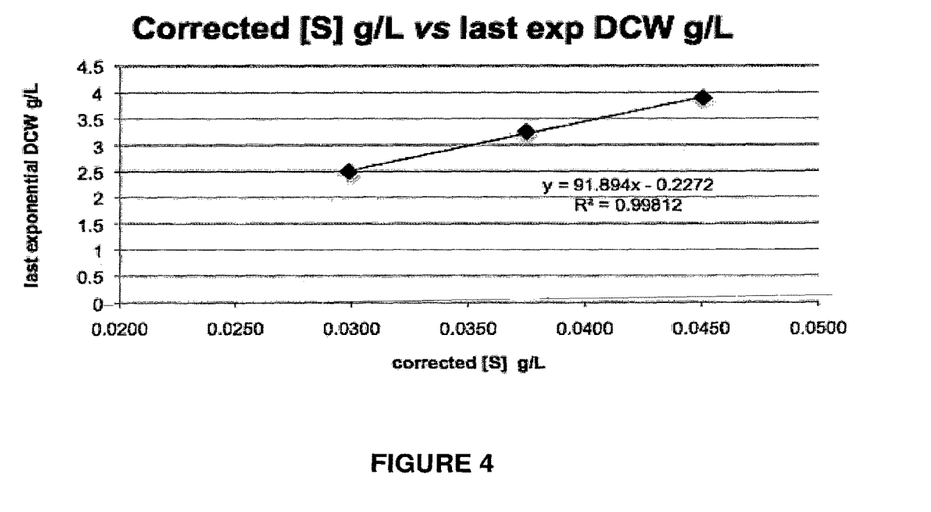
FIG. 4 shows graph of dry cell weight at which the cultures diverged from log phase growth against provision of sulfur.

However, it is clear from FIG. 2 that the cultures exit log phase growth earlier than they reach maximum dry weight. To calculate the amount of sulfur required to keep the cells in log phase growth, first the true amount of sulfur in the culture was calculated using the amount of biomass accumulated in the zero sulfur culture and the per dry cell weight sulfur requirements. Then, through plotting the dry cell weight at which the cultures diverged from log phase growth against the corrected sulfur content of the medium (FIG. 4) it was determined that only 91.9 mg of dry cell weight could be kept in log phase growth per mg of sulfur. This translates to 10.9 mg of sulfur being required per g of dry cell weight to keep the culture in log phase.

In cultures with densities of 45 g DCW/L this difference of around 8% amounts to an additional requirement of around 36 mg/L of sulfur or over 600 mg per liter of magnesium sulfate heptahydrate, thus demonstrating how the difference in approach is critical in medium design.

In order to determine a medium design to support log phase growth, this experiment was carried out for each of the nutrients in the medium. Thus, once in possession of the teaching in the present application a medium can be designed following this example, to support log phase growth of a variety of diatoms at different scales of fermentation.

Example 9

Instructions for Use of *Cyclotella cryptica*

The diatom, *Cyclotella cryptica* is cultured heterotrophically in a continuous culture in a 14 L fermentor. The medium composition is according to Pahl et al. (J Bioscience and Bioengineering 109: 235-239 (2010)) adjusted as per the methods of Example 8.)). The pH is maintained between 7.2 and 8.1 and the temperature between 23 C and 25 C. Culture dry cell weight is allowed to increase to at least 40 g dry weight/L at which time a 4 hr cycle of 10% harvest and refill of the culture is initiated. Silicate and fresh medium was fed to the culture as in Example 1. The EPA content of the biomass is expected to be at least 2% of dry cell weight. The harvested culture is concentrated by centrifugation to at least 150 g dry wt/L and freeze dried. The freeze dried biomass is extracted with ethanol and the lipids in the ethanol extract are transesterified to form the FAEEs. The FAEEs are partially concentrated by short path distillation (removal of colored compounds) and then the EPA-EE is purified to at least 60% purity by molecular distillation.

Example 10

Instructions for Use of *Phaeodactylum tricornutum*

The diatom *Phaeodactylum tricornutum* (an obligate photoautotroph) is first transformed according to the method of Apt et al. (U.S. Pat. No. 7,939,710) to give it the ability to grow heterotrophically using glucose as a source of energy and carbon. The transformed organism is cultured heterotrophically in a continuous culture in a 14 L fermentor using the culture medium described by Apt (U.S. Pat. No. 7,939,710) adjusted as per the methods of Example 8.). The pH is initially set and maintained above 8.0. The temperature maintained at 28 C and the agitation and aeration are adjusted to maintain a dissolved oxygen level of at least 40% of air saturation. The culture dry cell weight is allowed to increase to at least 20 g dry weight/L at which time a 4 hr cycle of 10% harvest and refill of the culture is initiated. Silicate and fresh medium was fed to the culture as in Example 1. The EPA content of the biomass is expected to be at least 2% of dry cell weight. The harvested culture is concentrated by centrifugation to at least 150 g dry wt/L and freeze dried. The freeze dried biomass is extracted with ethanol and the lipids in the ethanol extract are transesterified to form the FAEEs. The FAEEs are partially concentrated by short path distillation and then the EPA-EE is purified to at least 50% purity by molecular distillation.

Culture dry cell weight and harvest regime are chosen to produce biomass at a rate of at least 20 g dry weight/L/day. Medium conditions are chosen so that the biomass produced contains EPA at a level of greater than 2% of dry cell weight.

The invention claimed is:

1. A method of producing at least one highly unsaturated fatty (HUFA) or esters thereof, the method comprising the steps of:
   i) producing a diatom biomass by continuously culturing a diatom in a culture medium, wherein the volumetric production rate of biomass is at least 20 g dry weight/ L/day, and wherein the dilution rate of the culture medium maintains the diatom in log phase growth,
   ii) subjecting the diatom biomass to one or more extraction steps to extract the at least one HUFA or esters thereof from the biomass, thereby yielding an extract and
   iii) purifying the at least one HUFA or esters thereof from the extract.

2. The method of claim 1, wherein the HUFA is selected from the group consisting of eicosapentaenoic acid (EPA), docosahexaenoic acid (DHA), arachidonic acid (ARA) and any combination thereof.

3. The method of claim 2, wherein the diatom biomass contains EPA at a level of at least 2% of dry cell weight of the biomass.

4. The method of claim 1, wherein the mean volumetric production rate of biomass is at least 20 g dry weight/L/day over a period of at least a month.

5. The method of claim 1, wherein the diatom is a species of a genus selected from the group consisting of *Nitzschia, Cyclotella* and *Phaeodactylum*.

6. The method of claim 1, wherein the diatom is cultivated heterotrophically.

7. The method of claim 1, wherein the method includes replacement of at least 50% of the culture volume with fresh medium every 24 hr.

8. The method of claim 1, wherein the method further comprises the step of enriching the amount of HUFA or esters thereof in the extract obtained in step (iii).

9. The method of claim 8, wherein the enriched extract is incorporated in pharmaceutical products, medical foods, food additives, cosmetic products, dietary supplements, or feed additives.

* * * * *

UNITED STATES PATENT AND TRADEMARK OFFICE
CERTIFICATE OF CORRECTION

PATENT NO. : 10,377,983 B2  
APPLICATION NO. : 15/838772  
DATED : August 13, 2019  
INVENTOR(S) : Mark Humphrey Dines et al.

It is certified that error appears in the above-identified patent and that said Letters Patent is hereby corrected as shown below:

On the Title Page

At item (57), Line 7, "cmbodimcnt" should be -- embodiment --.

In the Claims

At Column 29, Line 26, "fatty (HUFA)" should be -- fatty acid (HUFA) --.

Signed and Sealed this  
Twenty-eighth Day of April, 2020

Andrei Iancu  
*Director of the United States Patent and Trademark Office*